(12) United States Patent
Huh (10) Patent No.: US 10,194,710 B2
(45) Date of Patent: Feb. 5, 2019

(54) HEADBAND HAVING INTEGRATED FUNCTIONAL CUSHION CASE

(71) Applicant: OTOS WING. CO., LTD., Seoul (KR)

(72) Inventor: Sung-Won Huh, Seoul (KR)

(73) Assignee: OTOS WING. CO., LTD., Seoul (KR)

( * ) Notice: Subject to any disclaimer, the term of this patent is extended or adjusted under 35 U.S.C. 154(b) by 149 days.

(21) Appl. No.: 15/309,622

(22) PCT Filed: Mar. 13, 2015

(86) PCT No.: PCT/KR2015/002478
§ 371 (c)(1),
(2) Date: Nov. 8, 2016

(87) PCT Pub. No.: WO2015/174626
PCT Pub. Date: Nov. 19, 2015

(65) Prior Publication Data
US 2017/0150770 A1   Jun. 1, 2017

(30) Foreign Application Priority Data
May 15, 2014  (KR) .......................... 10-2014-0058352

(51) Int. Cl.
*A42B 3/00*   (2006.01)
*A42B 3/32*   (2006.01)
*A61F 9/06*   (2006.01)
*A42B 3/08*   (2006.01)
(Continued)

(52) U.S. Cl.
CPC .............. *A42B 3/324* (2013.01); *A42B 3/085* (2013.01); *A42B 3/127* (2013.01); *A42B 3/142* (2013.01); *A61F 9/06* (2013.01)

(58) Field of Classification Search
CPC .......... A42B 3/324; A42B 3/085; A42B 3/127
See application file for complete search history.

(56) References Cited

U.S. PATENT DOCUMENTS 2,205,742 A * 6/1940 Bowers ................... A42B 3/145
                                                     2/418
5,950,245 A * 9/1999 Binduga ................. A42B 3/145
                                                     2/183
(Continued)

FOREIGN PATENT DOCUMENTS

KR    20-0290234       9/2002
KR    20-0321913 Y1    7/2003
(Continued)

OTHER PUBLICATIONS

International Search Report (Korean and English) and Written Opinion of the ISA (Korean) for PCT/KR2015/002478, ISA/KR, dated Jun. 25, 2015.

*Primary Examiner* — Richale Quinn
(74) *Attorney, Agent, or Firm* — Harness, Dickey & Pierce, P.L.C.

(57) ABSTRACT

The present invention relates to a headband including an adjustment band which is worn on a wearer's head and has the length adjusted; a support band which is connected to the adjustment band and is supported on the upper part of the wearer's head; and a length adjustment lever for adjusting the length of the adjustment band, wherein a cushion case of a flexible resilient material is integrally formed on the length adjustment lever.

5 Claims, 10 Drawing Sheets

(51) Int. Cl.
 A42B 3/12 (2006.01)
 A42B 3/14 (2006.01)

(56) References Cited

U.S. PATENT DOCUMENTS

| | | | | |
|---|---|---|---|---|
| 6,332,227 | B1* | 12/2001 | Fang | A42B 3/145 |
| | | | | 2/183 |
| 6,966,074 | B2 | 11/2005 | Huh | |
| 7,000,262 | B2* | 2/2006 | Bielefeld | A42B 3/145 |
| | | | | 2/418 |
| 7,174,575 | B1* | 2/2007 | Scherer | A42B 3/145 |
| | | | | 2/418 |
| 7,222,374 | B2* | 5/2007 | Musal | A42B 3/08 |
| | | | | 2/417 |
| 8,875,318 | B2 | 11/2014 | Huh | |
| 9,161,588 | B2* | 10/2015 | Chen | A42B 3/145 |
| 9,480,293 | B2* | 11/2016 | Pfanner | A42B 3/085 |
| 9,560,893 | B2* | 2/2017 | Gleason | A42B 3/142 |
| 9,907,348 | B2* | 3/2018 | Huh | A42B 3/14 |
| 2005/0138719 | A1* | 6/2005 | Huh | A42B 3/14 |
| | | | | 2/416 |
| 2006/0015986 | A1 | 1/2006 | Bielefeld | |
| 2012/0144565 | A1* | 6/2012 | Huh | A61B 90/35 |
| | | | | 2/421 |
| 2013/0111648 | A1* | 5/2013 | Huh | A42B 3/14 |
| | | | | 2/181 |

FOREIGN PATENT DOCUMENTS

KR    2012-0065632 A    6/2012
KR    2013-0049694 A    5/2013

* cited by examiner

HEADBAND HAVING INTEGRATED FUNCTIONAL CUSHION CASE

CROSS REFERENCE TO RELATED APPLICATIONS

This application is a 371 U.S. National Stage of International Application No. PCT/KR2015/002478, filed Mar. 13, 2015, which claims the benefit of and priority to Korean Patent Application No. 10-2014-0058352, filed May 15, 2014. The entire disclosures of the above applications are incorporated herein by reference.

TECHNICAL FIELD

The present invention relates to a headband, and more particularly, to a headband having an integrated functional cushion case installed in a welding mask (a welding face shield), a safety face shield, a hard hat, a helmet, and a medical helmet, capable of increasing wearability and simultaneously preventing the headband from falling off and being separated by coming into gradual contact when the headband is worn on an occipital region and increasing ventilation and airing to minimize perspiration at the head of a wearer.

BACKGROUND ART

Generally, industrial safety equipment such as a welding mask (a welding face shield), a safety face shield, a hard hat, a helmet or the like are products used in various industrial fields, and a medical head guard, a safety hat, a medical helmet or the like are medical supplies for preventing an accident which may occur while a worker or a wearer is working.

A welding mask among the industrial safety equipment described above is used for preventing various accidents such as sparking of a parent metal toward the face of a worker caused by a strong flash and instantaneous high heat and resistance which occur during a welding operation.

When a worker wears a welding mask on his or her head as described above, the vision and face of the worker may be protected from an accident such as sparking of a parent metal for welding toward the face of the worker while the worker is working.

Meanwhile, the welding mask described above includes a welding face shield for protecting the face of a worker and a headband for being worn on the head of a worker.

That is, the welding mask includes a welding face shield with a transparent window for protecting the vision and face of a worker from an accident while being worn and a headband provided inside the welding face shield worn on the head of the worker for fixing the welding face shield thereto.

Figure 1:
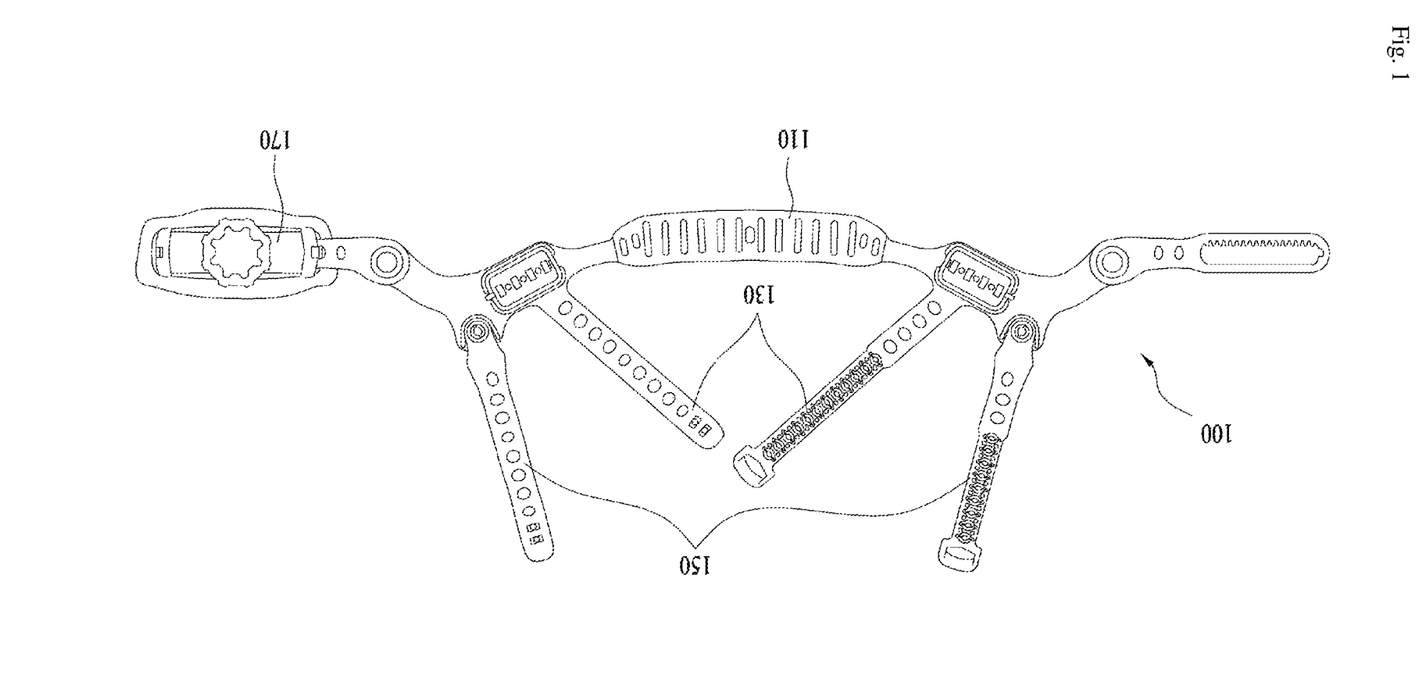
FIG. 1 is a planar figure schematically illustrating a headband according to a conventional technology.
Figure 2:
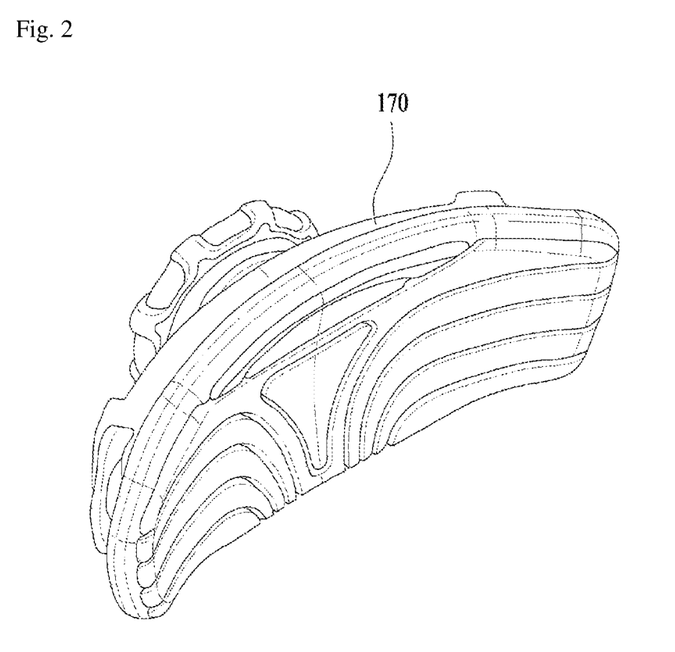
FIG. 2 is a perspective view schematically illustrating a length adjusting lever of the headband according to the conventional technology.
Figure 3:
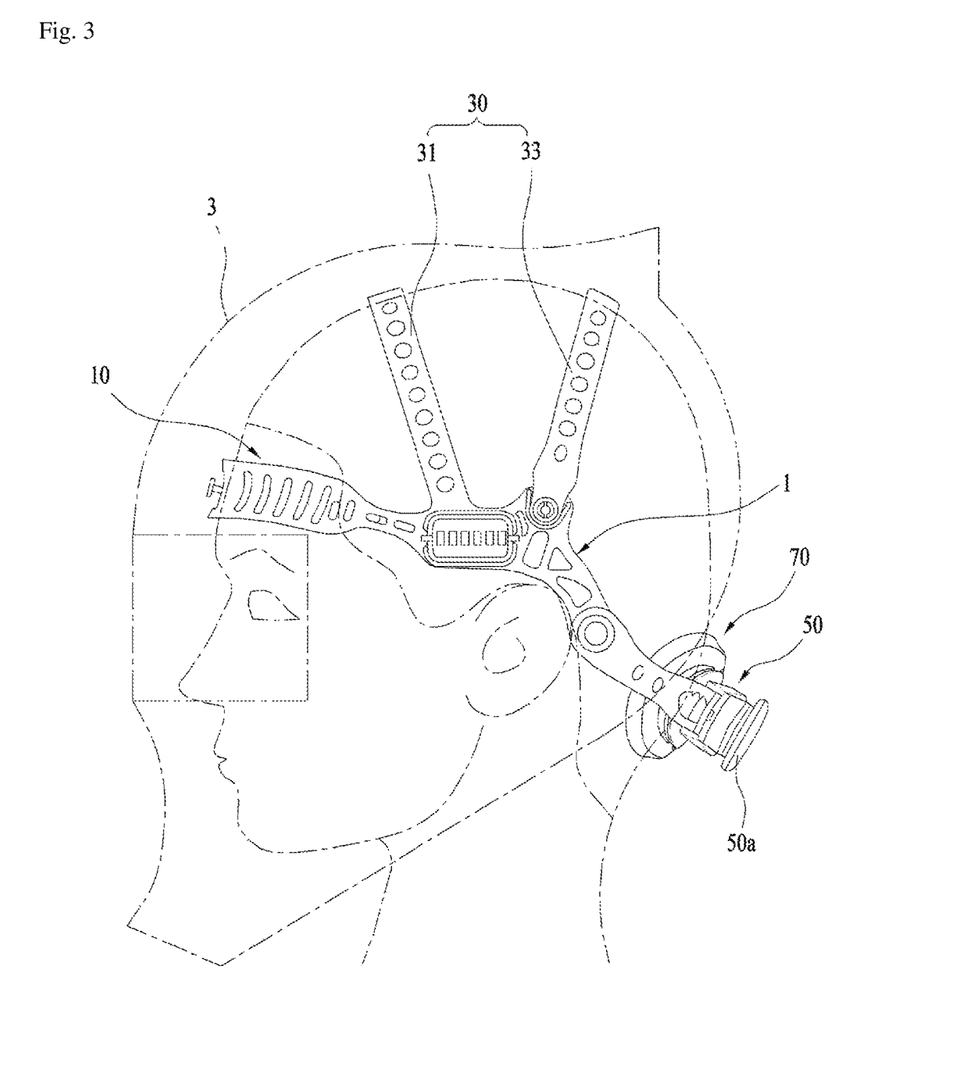
FIG. 3 is a side view schematically illustrating a worn state of the headband according to the conventional technology.

As shown in FIGS. 1 to 3, the headband described above includes a first band portion 110 which surrounds a perimeter of the head of a wearer and is formed to be in close contact with the forehead, and a second band portion 130 and a third band portion 150 for surrounding the front region and occipital region of the head.

Here, a headband 100 includes a length adjusting lever 170 configured to touch the occipital region of the wearer, and the length adjusting lever 170 is connected to an end portion of the first band portion 110 using a length adjusting band (not shown).

Here, as a general technology in the art, the length adjusting lever 170 is connected while both end portions of the length adjusting band connected to the end portion of the first band portion 110 are inserted in left and right sides and an elongated hole with sawteeth is formed at the length adjusting band to be coupled with the length adjusting lever.

Meanwhile, the length adjusting lever 170 includes a cushion member adhered to an inner surface thereof to come into close contact with the occipital region of a worker.

Since the cushion member is provided at the inner surface of the length adjusting lever as described above, the cushion member surrounds the occipital region of a worker while the worker wears the headband, thereby providing convenience of wearing a welding mask including the headband and simultaneously providing comfortability.

As described above, the length adjusting lever provided at the headband installed in industrial safety equipment, such as a welding mask (a welding face shield), a safety face shield, a hard hat, a helmet and the like, or medical supplies such as a medical head guard, a safety hat, a medical helmet and the like, is configured to simply adjust a length of a band portion to come into close contact with the head of a wearer and includes a plastic material due to a structure thereof, and the structure is vulnerable to absorption of sweat at the occipital region of the wearer. Due to this, during a long welding operation, the occipital region is beaded with sweat and the wearer feels uncomfortable.

Also, since the length adjusting lever becomes slippery, the headband falls off and separated which reduces wearability, and humidity occurs inside the headband in such a way that a smell such as an odor and the like is generated.

Also, since the occipital region of a wearer is pressurized while the wearer works for a long time while wearing industrial safety equipment, such as a welding mask and the like, and medical supplies, such as a medical helmet and the like, a headache, discomfort and the like are caused.

PRIOR ART DOCUMENT

Patent Document

Korean Patent Registration No. 10-1253075

DISCLOSURE OF INVENTION

Technical Problem

The present invention provides a headband having an integrated functional cushion case capable of improving wearability when the headband is worn due to a cushion case including a flexible material and an elastic material having elasticity and integrated with a length adjusting lever of the headband configured to touch the occipital region of a wearer, sequentially/gradually come into contact with the occipital region of the wearer to be easily worn on the occipital region of the wearer and be in close contact therewith, simultaneously buffer pressure to the headband or a movement thereof using an elastic hole which passes therethrough, be closely worn on the head while simultaneously maintaining a close contact state regardless of a shape and size of the head of the wearer, minimize and buffer pressure while being worn due to a bent portion being formed at an edge end portion of the cushion case, strongly maintain a state of being worn on the head by preventing the headband from falling off and separating through different bending moduli for each position in the cushion case, and minimize perspiration while the wearer works for a long time through easy ventilation and airing inside the headband while the headband is worn by a vent groove being formed at an inner surface of the cushion case.

Technical Solution

One aspect of the present invention provides a headband including an adjustable band configured to be worn on a head of a wearer and adjustable in length, a supporting band connected to the adjustable band and configured to support a top of the head of the wearer, and a length adjusting lever configured to adjust a length of the adjustable band. Here, a cushion case including an elastic material extends from the length adjusting lever and is integrated therewith.

Here, the cushion case may include a mounting member formed at an inner surface of the length adjusting lever and an elastic member formed at an edge of the mounting member.

Here, at least one elastic hole may be formed at the elastic member to pass therethrough, and may be configured to come into gradual contact with an occipital region of the wearer when the headband is worn.

Here, at least one elastic hole may be sequentially/gradually formed at both sides of the elastic member in a longitudinal direction thereof to pass therethrough, and may be configured to come into gradual contact with an occipital region of the wearer when the headband is worn.

Meanwhile, in the cushion case, a bending modulus R1 formed at both ends of a center thereof in a longitudinal direction thereof may be formed to be greater than a bending modulus R2 formed at both ends of a lower portion in the longitudinal direction, or the elastic member is formed at the mounting member to be bent in an L shape.

Also, a vent groove may be formed at a center of an inner surface of the mounting member.

Here, a cushion member including an elastic material and a vent portion formed at a center thereof may be provided at an inner surface of the cushion case, and the cushion member may be formed in a shape corresponding to the mounting member and the elastic member.

Here, a bent portion bent by a certain angle may be formed at an edge end of the cushion member.

Meanwhile, an edge of the cushion member may be formed in a stepped shape bent several times.

Also, a cushion portion may be formed to protrude in a U shape at each of both sides of a center of the vent portion of the cushion member.

Also, at least one rib may be formed to radially protrude at a position in the cushion member corresponding to a position of the elastic member.

Advantageous Effects

As described above, the present invention including the configuration described above provides effects of being easily and conveniently detachable from industrial safety equipment to which a headband is applied, easily coming into contact with the occipital region of a wearer to increase wearability, coming into comfortable contact with the occipital region due to a flexible and elastic material, easily coming into contact with the occipital region of the wearer by sequentially/gradually coming into contact with the occipital region of the wearer, being in close contact with the head of the wearer and simultaneously strongly maintaining a close contact state regardless of a shape and size of the head, buffering strong pressure and movement and simultaneously minimizing pressure while being worn on, easily ventilating and airing an inside of the headband by minimizing a close contact with the occipital region of the wearer, and minimizing perspiration at the head while working due thereto, thereby increasing working efficiency and effectiveness.

BEST MODE FOR INVENTION

Hereinafter, exemplary embodiments of the present invention will be described in detail with reference to the attached drawings. Also, the embodiments are not intended to limit the scope of the present invention but are merely provided as examples, and may be variously changed without departing from the technical concept of the present invention.

Figure 4:
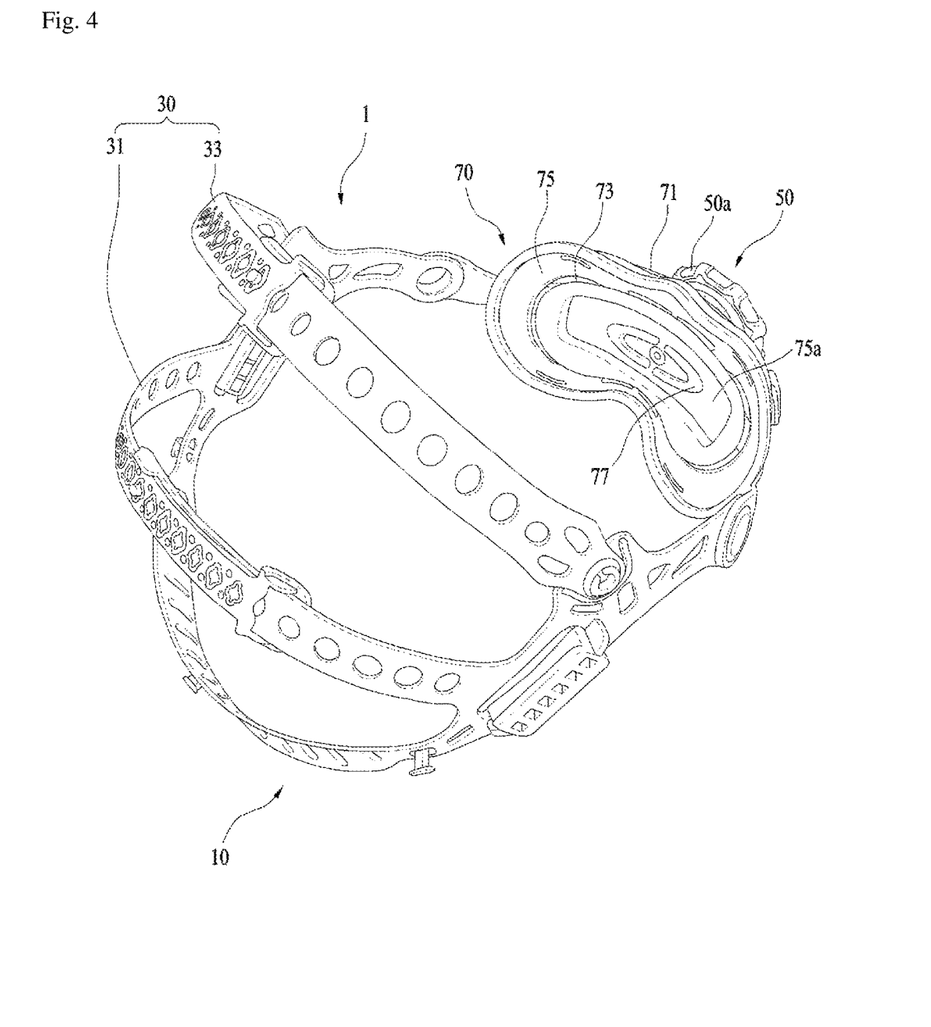
FIG. 4 is a perspective view schematically illustrating a headband having an integrated functional cushion case according to the present invention.
Figure 5:
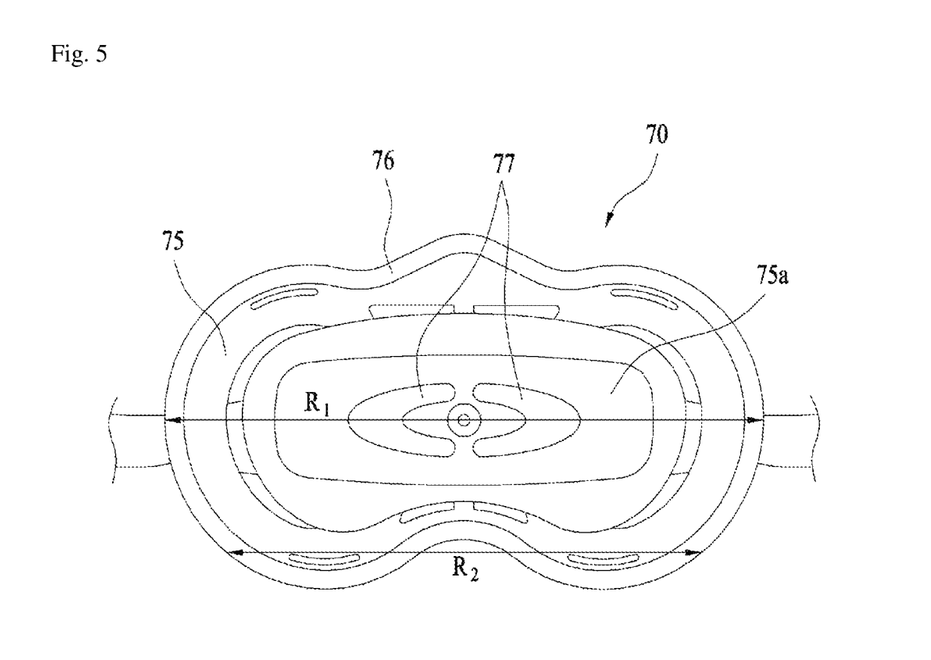
FIG. 5 is a front view schematically illustrating a functional cushion according to the present invention.
Figure 6:
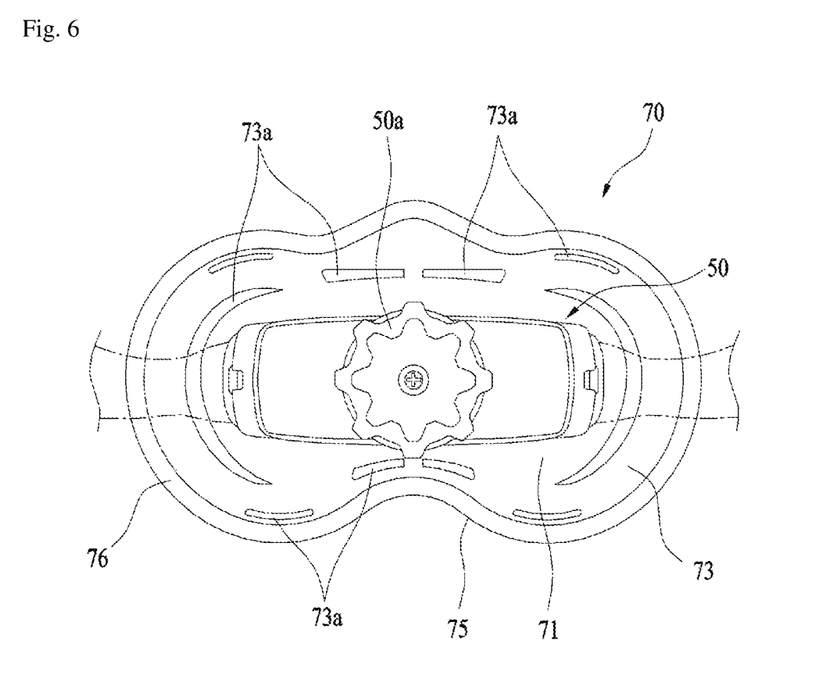
FIG. 6 is a rear view schematically illustrating the functional cushion according to the present invention.
Figure 7:
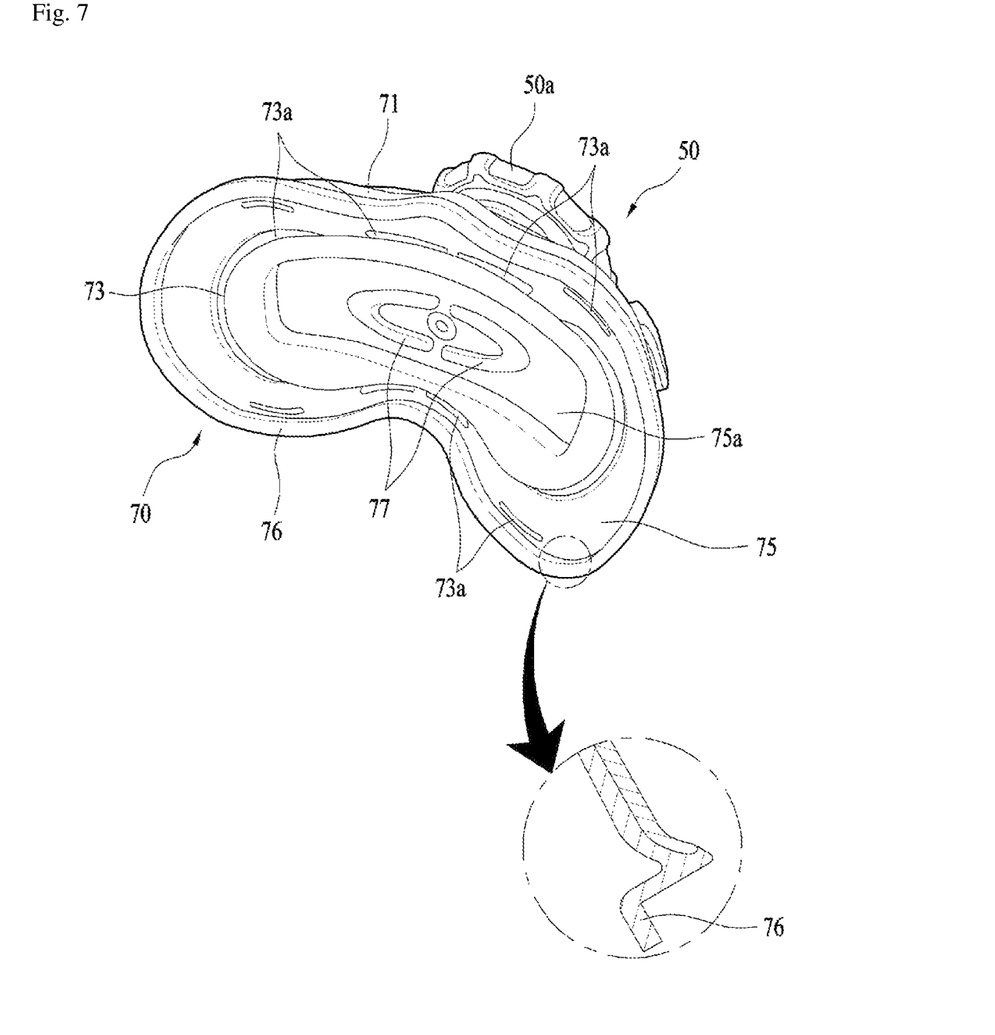
FIG. 7 is a perspective view schematically illustrating the functional cushion according to the present invention.
Figure 8:
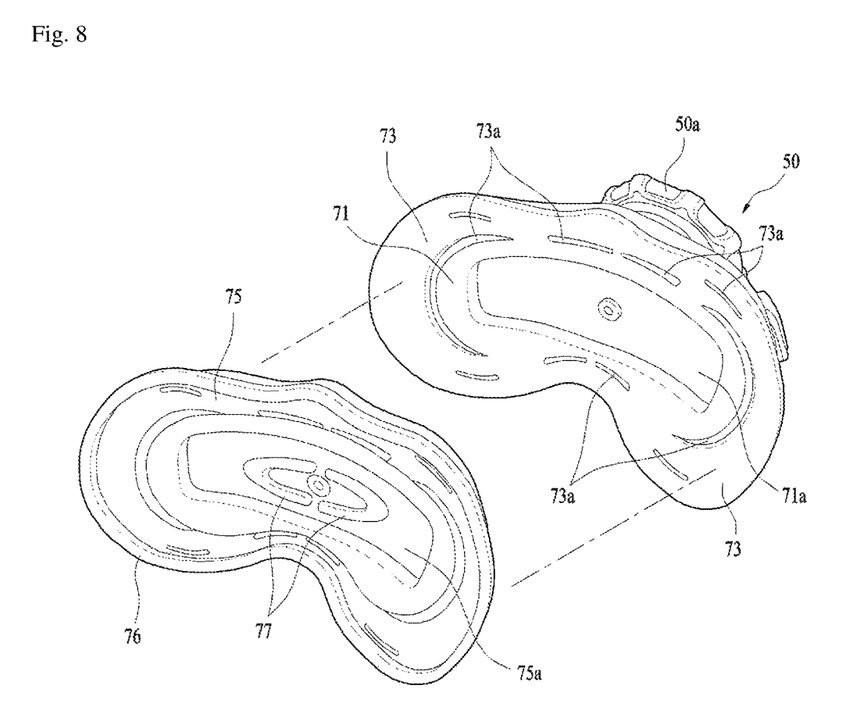
FIG. 8 is an exploded perspective view schematically illustrating the functional cushion according to the present invention.
Figure 9:
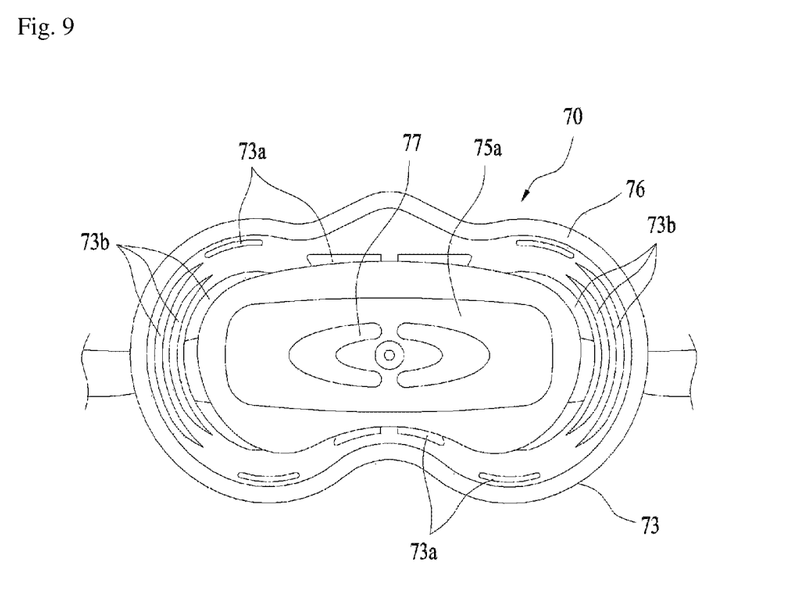
FIG. 9 is a front view schematically illustrating a functional cushion according to another embodiment of the present invention.
Figure 10:
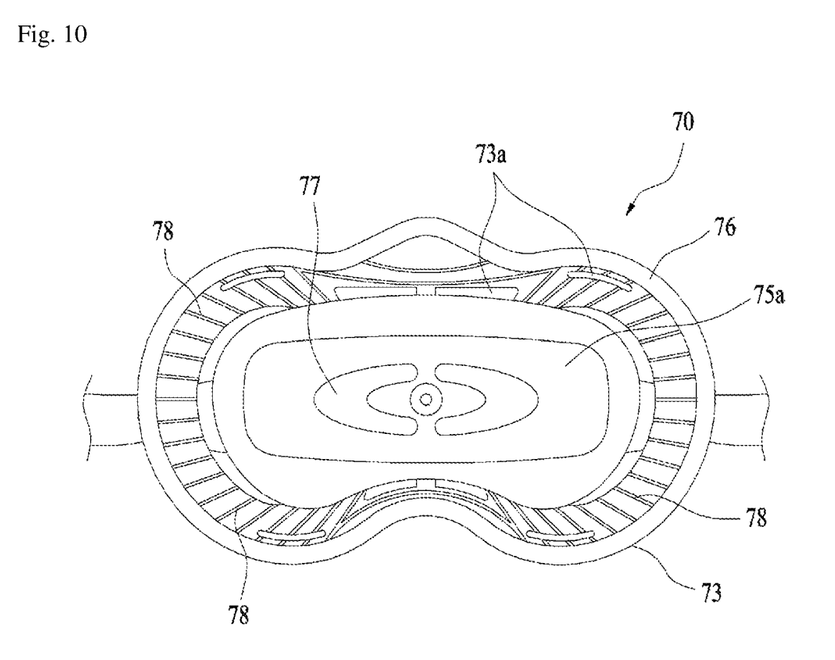
FIG. 10 is a front view schematically illustrating a functional cushion according to still another embodiment of the present invention.
Figure 11:
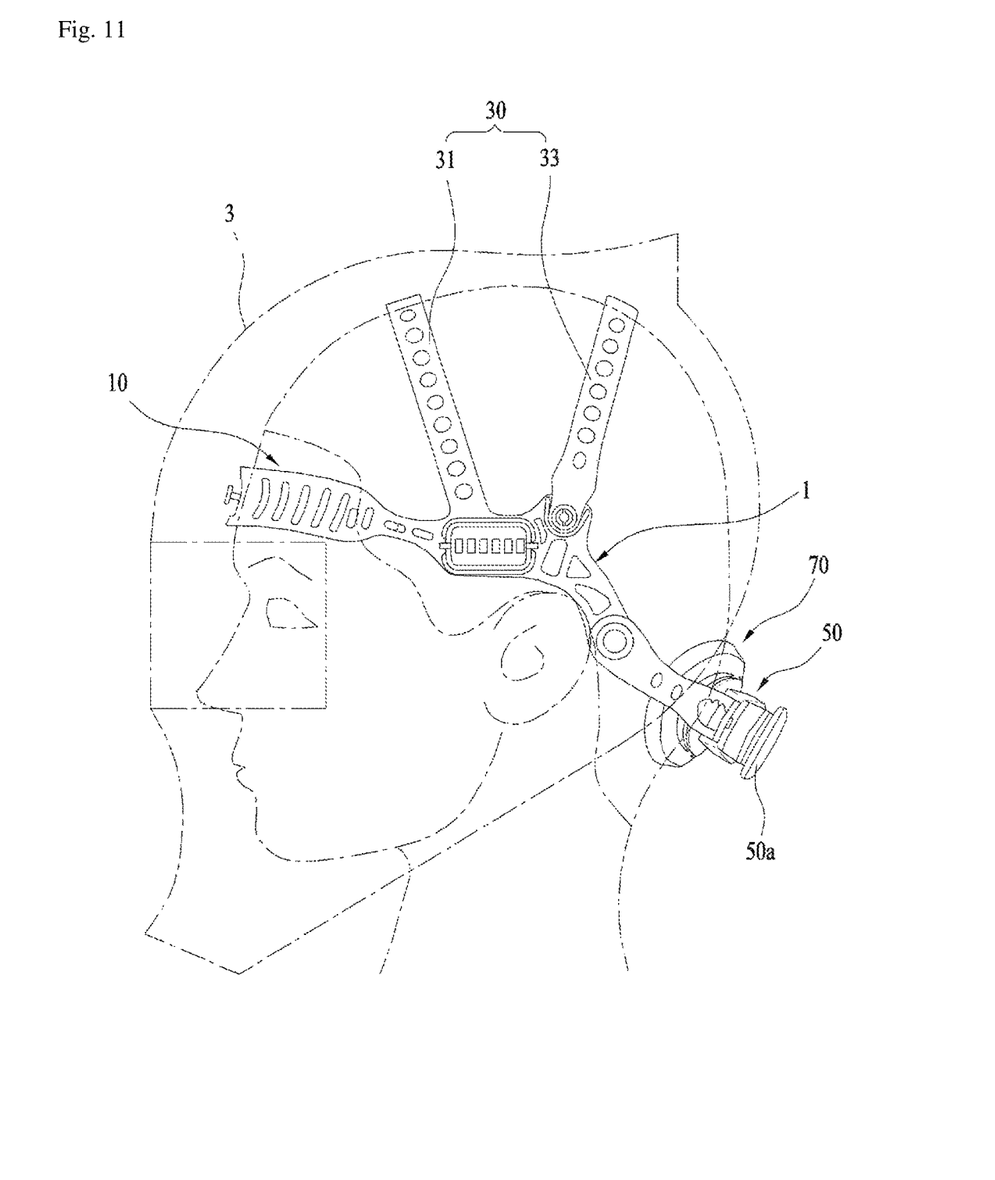
FIG. 11 is a side view schematically illustrating an appearance of a worn welding mask to which the headband having an integrated functional cushion case according to the present invention is applied.

FIG. 4 is a perspective view schematically illustrating a headband having an integrated functional cushion case according to the present invention, FIG. 5 is a front view schematically illustrating a functional cushion according to the present invention, FIG. 6 is a rear view schematically illustrating the functional cushion according to the present invention, FIG. 7 is a perspective view schematically illustrating the functional cushion according to the present invention, FIG. 8 is an exploded perspective view schematically illustrating the functional cushion according to the present invention, FIG. 9 is a front view schematically illustrating a functional cushion according to another embodiment of the present invention, FIG. 10 is a front view schematically illustrating a functional cushion according to still another embodiment of the present invention, and FIG. 11 is a side view schematically illustrating an appearance of a worn welding mask to which the headband having an integrated functional cushion case according to the present invention is applied.

As shown in the drawings, a headband 1 according to the present invention is applied to various types of industrial safety equipment, such as a welding mask 3 (a welding face shield), a safety face shield, a hard hat, a helmet and the like, and medical supplies, such as a medical head guard, a safety hat, a medical helmet and the like, to prevent accidents while working. Since industrial safety equipment, medical supplies, and a detailed installation structure of the headband 1 on industrial safety equipment and medical supplies correspond to a general technology, descriptions thereof will be omitted hereafter.

The headband 1 includes an adjustable band 10, a supporting band 30, and a length adjusting lever 50.

The adjustable band 10 is worn on the head of a wearer, formed in an annular shape surrounding the forehead to an occipital region of the wearer, and configured to be adjustable in length according to a size and a perimeter of the head of the wearer.

For this, an elongated hole (not shown) in a saw-toothed slot is formed at each of both ends of the adjustable band 10 and coupled to the length adjusting lever 50 to adjust the length of the adjustable band 10.

Here, a coupling hole (not shown) for coupling with the welding mask 3 is formed at each of the both sides of the adjustable band 10 positioned at the forehead of the wearer, and the welding mask 3 is rotatably coupled to the coupling hole using a hinge (not shown).

The supporting band 30 extends on the adjustable band 10 and is positioned at an upper portion of the head of the wearer to support the adjustable band 10 while the wearer is wearing the headband 1.

For this, the supporting band 30 includes a first supporting band 31 provided in front of the adjustable band 10 and positioned at an upper portion of a front region of the wearer and a second supporting band 33 provided behind of the first supporting band 31 and positioned at the top of the wearer.

According to one embodiment of the present invention, the two supporting bands 31 and 33 are formed at the adjustable band 10 to extend therefrom, but the number of the supporting bands 30 is not limited thereto and is variously changeable. Also, a position of the supporting band 30 formed at the adjustable band 10 to extend therefrom is variously changeable.

The both ends of the adjustable band 10 are inserted into and coupled to the length adjusting lever 50, and the length of the adjustable band 10 is adjusted by rotating a lever 50a.

That is, the length adjusting lever 50 is for adjusting the length of the adjustable band 10 to be adequate for the size and perimeter of the head of the wearer. The both ends of the adjustable band 10 are inserted into and coupled to left and right sides of the length adjusting lever 50. The length of the adjustable band 10 is finely adjusted by forwardly rotating and backwardly rotating the lever 50a.

Here, since a configuration for adjusting the length of the adjustable band 10 using the length adjusting lever 50 provided at the headband 1 according to the present invention is ordinary skill in the art, a detailed description thereof will be omitted.

Meanwhile, the length adjusting lever 50 is positioned at the occipital region of the wearer. That is, the length adjusting lever 50 is connected to the both ends of the adjustable band 10 and positioned at a lower portion of the occipital region of the head of the wearer to prevent a center of gravity from being positioned in front while the headband 1 is worn. For this, an inner surface of the length adjusting lever 50 is formed to be in close contact with the lower portion of the occipital region.

As described above, since the length adjusting lever 50 is worn in close contact with the lower portion of the occipital region of the head of the wearer, the welding mask 3 and the like are prevented from falling off toward the front.

Here, a cushion case 70 is formed at the length adjusting lever 50. That is, the cushion case 70 is formed to extend and be bent inward to enable the occipital region of the wearer to be mounted thereon, and is integrated with the length adjusting lever 50.

Here, the cushion case 70 may be formed to be larger than a size of the length adjusting lever 50 and to have an inner surface formed to be concavely rounded toward the center thereof to correspond to a shape of the occipital region of the wearer, but is not limited thereto.

Meanwhile, the cushion case 70 includes a mounting member 71 and an elastic member 73. That is, the cushion case 70 includes the mounting member 71 formed at the inner surface of the length adjusting lever 50 and the elastic member 73 formed at an edge of the mounting member 71.

Here, the cushion case 70 may be formed of a flexible elastic material to be modified to correspond to the size and shape of the head of the wearer, and the mounting member 71 and the elastic member 73 of the cushion case 70 may be manufactured through double injection, but the present invention is not limited thereto.

In one embodiment of the present invention, the cushion case 70 is integrated with the length adjusting lever 50 and extends therefrom. However, the cushion case 70 may be installed to be separably coupled to the length adjusting lever 50.

The elastic member 73 of the cushion case 70 includes at least one elastic hole 73a passing therethrough. That is, the elastic member 73 includes a plurality of such elastic holes 73a passing therethrough to enable the cushion case 70 worn on the occipital region of the wearer to be bent in various directions, such as upward, downward, leftward, rightward, and the like, and at various angles to be in close contact with the occipital region of the wearer while the headband 1 is worn.

Here, the elastic holes 73a are formed in a slot shape at each of a top and bottom of the center and a top and bottom of both sides thereof to increase elasticity of the elastic member 73.

As described above, due to the elastic holes 73a formed at the functional cushion case-integrated headband 1 according to the present invention, the cushion case 70 is may be flexibly and elastically modified in shape to be in close contact with the occipital region of the wearer regardless of the size, the shape, a wearing direction, and the like thereof while being worn, and to perform a function of pressurizing and buffering the headband 1 while the wearer working for a long time.

Here, the elastic holes 73a may increase elasticity of the elastic member 73 and perform the function of pressurizing and buffering the headband 1 to be in close contact with the head of the wearer regardless of the shape and size thereof and perform as a through hole to increase permeability and ventilation for the head of the wearer while the headband 1 is worn.

In one embodiment of the present invention, the elastic hole 73a is formed to pass through each of the top and bottom of the center of the elastic member 73 and the top and bottom of the both sides, but the number and positions of the elastic holes 73a are not limited thereto and may be variously modified.

As described above, the elastic hole 73a is formed to pass through the cushion case 70 in such a way that left and right sides of the cushion case 70 are flexibly modified according to the shape and size of the head of the wearer and the length of the adjustable band 10 is modified to correspond to the shape and size of the head of the wearer.

Here, in one embodiment of the present invention, the elastic hole 73a formed to pass through the elastic member 73 is formed in a slot shape. However, when the elastic member 73 formed to extend and be integrated with the mounting member 71 is flexibly modifiable in shape, the elastic hole 73a may have various forms and shapes such as a circle, oval, semicircle, and the like.

Meanwhile, in one embodiment of the present invention, the elastic hole 73a is formed to pass through each of the top and bottom of the center of the elastic member 73 and the top and bottom of the both sides thereof to increase the flexibility of the elastic member 73. However, as shown in FIG. 9, elastic holes 73b may be formed to pass through the elastic member 73 to be sequentially/gradually arranged at both sides in a longitudinal direction thereof to increase flexibility of the elastic member 73 in such a way that the cushion case 70 may come into gradual contact with the occipital region of the wearer while the headband 1 is worn.

In the embodiment, the elastic holes 73b have a semicircular shape. However, the elastic holes 73a may have a slot shape.

Also, in the embodiment, the elastic holes 73b are sequentially/gradually formed to pass through the elastic member 73 and arranged in a shape to enable a length thereof to be gradually longer from the inside to the outside. However, the elastic holes 73b may be arranged in a shape to enable the length thereof to be gradually shorter from the inside to the outside, may be arranged in a shape to enable the length thereof to be the same from the inside to the outside, may be arranged in a shape to enable a short length and a long length to alternate consecutively from the inside to the outside, and may be arranged in a shape to enable a long length and a short length to alternate consecutively from the inside to the outside, but are not limited thereto.

Meanwhile, the cushion case 70 is formed to enable a bending modulus R1 at the center to be greater than a bending modulus R2 at the lower portion. That is, in the cushion case 70, the bending modulus R1 at both longitudinal ends of the center of the inner surface, which is formed in a round shape to be concave toward the center portion to correspond to the shape of the occipital region while being in close contact with the head of the wearer, is formed to be greater than the bending modulus R2 at both longitudinal ends of the lower portion, which is in close contact with the neck at a lower end of the occipital region of the wearer.

In other words, the bending modulus R1 at the center of the cushion case 70 at which the mounting member 71 and the elastic member 73 formed at the edge of the mounting member 71 are positioned is formed to be greater than the bending modulus R2 at the lower portion of the cushion case 70 at which the elastic member 73 is positioned.

As described above, since the bending modulus R1 at the center of the cushion case 70 positioned at the occipital region of the wearer is formed to be greater than the bending modulus R2 at the lower portion positioned near the neck of the wearer, it is possible to prevent the headband 1 from falling off from the head of the wearer and to prevent the cushion case 70 from deviating and falling off of the head of the wearer while the headband 1 is worn.

Here, the center of the cushion case 70 may be formed with the bending modulus R1 adequate for the occipital region of the wearer, and the bending modulus R2 at the lower portion thereof may be formed to be smaller than the bending modulus R1 at the center but may have a curve for preventing the headband 1 from falling off of the head of the wearer, but the present invention is not limited thereto.

In one embodiment of the present invention, the cushion case 70 is formed in a rounded shape entirely concave toward the center corresponding to the shape of the occipital region of the wearer. However, the elastic member 73 may be formed at the mounting member 71 of the cushion case 70 to be bent in an approximate L shape to be closely worn on the occipital region of the wearer regardless of the shape and size thereof.

That is, the elastic member 73 formed at the edge of the mounting member 71 of the cushion case 70 is formed at the mounting member 71 to be bent by a certain angle to enable a cross section thereof to be formed in an approximate L shape to be closely worn on the occipital region of the wearer regardless of the shape and size thereof.

Here, the elastic member 73 is formed at the edge of the mounting member 71 to be bent in an approximate L shape. However, a bending angle of the elastic member 73 at the mounting member 71 is not limited thereto and may be variously modified.

In the embodiment, the elastic member 73 formed at the edge of the mounting member 71 of the cushion case 70 is bent in the L shape. However, the elastic member 73 formed at the edge of the mounting member 71 may be formed to be bent multiple times and may be formed in various other shapes as long as it is possible to be worn on the occipital region of the wearer regardless of the shape and size thereof and it is easy to maintain a close contact state after being worn thereon.

Meanwhile, a vent groove 71a is formed in the center of an inner surface of the mounting member 71. That is, the vent groove 71a is formed in a quadrangular shape and is formed at the center of the inner surface of the mounting member 71 of the cushion case 70.

As described above, the cushion case 70 extends and is integrated with the inner surface of the length adjusting lever, thereby maximizing a range of the occipital region that the cushion case 70 touches. Also, the vent groove 71a is formed at the center of the inner surface of the mounting member 71 of the cushion case 70, thereby minimizing an area of the cushion case 70, which extends and is integrated with the inner surface of the length adjusting lever, touching the occipital region while the headband 1 is worn on. That is, the whole inner surface of the mounting member 71 does not touch the occipital region of the wearer and a part of the mounting member 71 except the vent groove 71a formed at a curved portion, which is an edge portion of the vent groove 71a, is formed to touch the occipital region, thereby preventing a vulnerable place caused by the vent groove 71a and obtaining ventilation and airing effects.

As described above, since the vent groove 71a is formed between the occipital region of the wearer and the mounting member 71 touching the occipital region, ventilation and airing for the headband 1, the inside of the welding mask 3, and the head of the wearer are facilitated when industrial safety equipment, such as a welding mask and the like, and medical supplies, such as a medical helmet and the like, are worn, thereby increasing ventilation and airing properties for the head of the wearer such as minimizing perspiration while working.

In one embodiment of the present invention, the vent groove 71a in a groove shape is formed at the inner surface of the mounting member 71 to increase ventilation and airing properties while the headband 1 is worn. However, a plurality of such vent grooves 71a may be formed in a groove shape or a slot shape at the inner surface of the mounting member 71 to increase the ventilation and airing properties while the headband 1 is worn on. The vent groove 71a may be formed in an embossed shape at the inner surface of the mounting member 71, and may be formed in various other shapes as long as it is easy to increase the ventilation and airing properties.

Also, in one embodiment of the present invention, although the vent groove 71a in the quadrangular shape is formed at the inner surface of the mounting member 71, the vent groove 71a may be formed in a circular shape, a triangular shape, or an elliptical shape, and the form, shape, and size of the vent groove 71a may be diversely modified.

Meanwhile, a cushion member 75 including a flexible material is provided at the inner surface of the cushion case 70. That is, the cushion member 75 including a flexible material having elasticity is formed in a shape corresponding to the shapes of the mounting member 71 and the elastic member 73 and is provided at the inner surface of the cushion case 70.

Since the cushion member 75 including a flexible material is provided at the inner surface of the cushion case 70 as described above, the cushion member 75 including a flexible material is in close contact with the head of the wearer to be easily worn thereon and prevents pressure and pressurization to the head of the wearer to provide comfortable fit while the headband 1 is worn.

Here, the cushion member 75 provided at the cushion case 70 is configured to be attached to the inner surfaces of the mounting member 71 and the elastic member 73. For this, the cushion member 75 includes a vent portion 75a formed at the center thereof in a shape corresponding to the shape of the vent groove 71a formed at the center of the mounting member 71 and corresponding to the vent groove 71a, and an opening (not shown) formed in a shape corresponding to the shape of the elastic member 73 formed at the edge of the mounting member 71 corresponding to the elastic hole 73a.

That is, the cushion member 75 provided at the inner surface of the mounting member 71 of the cushion case 70 includes the vent portion 75a at the center thereof and is coupled to the mounting member 71 and installed thereon. The vent portion 75a is formed to correspond to the vent groove 71a of the mounting member 71 and is inserted and installed in the vent groove 71a of the mounting member 71 when the cushion member 75 is installed at the cushion case 70.

Here, the cushion member 75 may be formed to correspond to the shapes of the mounting member 71 and the elastic member 73 which form the cushion case 70. When the shapes of the mounting member 71 and the elastic member 73 of the cushion case 70 are changed, the cushion member 74 may be formed to correspond thereto, but the present invention is not limited thereto.

Meanwhile, a cushion portion 77 is formed to protrude in a U shape at each of both sides of the center of the cushion member 75, that is, at the center of the vent portion 75a formed in the shape corresponding to the vent groove 71a of the mounting member 71.

Since the cushion portion 77 is formed to protrude from each of both sides of the center of the vent portion 75a of the cushion member 75 as described above, buffering between the occipital region of the wearer partially inserted into the vent portion 75a and the inner surface of the vent portion 75a may be performed while the headband 1 is worn.

In one embodiment of the present invention, the cushion portion 77 is formed in the U shape. However, as long as buffering between the occipital region of the wearer partially inserted in the vent portion 75a and the inner surface of the vent portion 75a is easily performed while the headband 1 is worn, the shape of the cushion portion 77 is not limited thereto and may be modified in various other shapes.

Here, a bent portion 76 bent by a certain angle is formed at an edge end of the cushion member 75. That is, the bent portion 76 is formed to be bent by a certain angle at the edge end of the cushion member 75 of the cushion case 70 touching the head of the wearer such as the occipital region when the headband 1 is worn.

Since the bent portion 76 is formed at the edge end of the cushion member 75 of the cushion case 70 and touches the head of the wearer first when the headband 1 is worn on the head of the wearer as described above, a buffering effect is obtained.

Meanwhile, the edge of the cushion member 75 of the cushion case 70 may be formed in a stepped shape which is bent several times.

Since the edge of the cushion case 70 configured to touch the occipital region of the wearer is formed in the stepped shape bent several times as described above, a portion formed in the stepped shape at the edge of the cushion case 70 touching the head of the wearer first is gradually worn on the head of the wearer in such a way as to be folded and in close contact and the like therewith to increase wearability regardless of the size and shape of the head of the wearer when the headband 1 is worn.

In the embodiment, the edge of the cushion member 75 of the cushion case 70 is formed in the stepped shape bent several times in vertical and horizontal directions. However, as long as the portion touching the head of the wearer first when worn is folded and in close contact to be easily gradually worn on the head of the wearer, a portion in a zigzag shape or a bellows shape bent several times may be formed at the edge of the cushion member 75 of the cushion case 70.

Here, as shown in FIG. 10, a rib 78 is formed to protrude at the cushion member 75 provided at the inner surface of the cushion case 70. That is, at least one rib 78 which is formed to protrude radially at a position in the cushion member 75 corresponding to a position of the elastic member 73 of the cushion case 70.

Since the rib 78 is formed at the cushion member 75 as described above, durability of the cushion member 75 and the cushion case 70 may be increased and wearability may be increased while simultaneously the cushion case 70 may be prevented from falling off.

In one embodiment, a plurality of such ribs 78 are formed to radially protrude at the cushion member 75. However as long as it is possible to increase the durability of the cushion member 75 and the cushion case 70 and increase wearability while simultaneously preventing the cushion case 70 from falling off, the number or shape of the rib 78 may be variously changed.

In the embodiment, the cushion member 75 including a flexible material is provided at the inner surface of the cushion case 70. However, only the cushion case 70 may be provided without the cushion member 75.

Also, in the embodiment, the cushion member 75 includes a flexible material. As long as it is easy to enable the cushion member 75 to be in close contact with and easily worn on the head of the wearer while the headband 1 is worn while simultaneously providing a comfortable fit by preventing pressure and pressurization to the head of the wearer, the material of the cushion member 75 is not limited thereto.

Also, the cushion member 75 according to the embodiment may be formed at the inner surface of the cushion case 70 through double injection molding, but the present invention is not limited thereto.

Meanwhile, as shown in FIG. 11, the headband 1 having an integrated functional cushion case according to the present invention includes the cushion case 70 at the inner surface of the length adjusting lever 50 having a general structure for adjusting a length of an adjustable band to touch the occipital region of the wearer over a wide area. Here, the elastic hole 73a is formed at the cushion case 70 and flexibly and elastically modified in shape, thereby being easily worn and fixed when applied to industrial safety equipment, such as a welding mask and the like, and medical supplies, such as a medical helmet and the like. Also, pressure and pressurization of the headband 1 may be minimized due to the cushion member 75 provided at the cushion case 70, thereby the headband 1 may be simply and easily utilized. Also, the vent groove 71a is formed at the inner surface of the cushion case 70 to increase ventilation and airing inside the headband 1.

Although particular embodiments of the present invention have been described, one of ordinary skill in the art should easily understand that various modifications and changes can be made without departing from the concept of the present invention defined by the scope of the following claims.

DESCRIPTION OF REFERENCE NUMERALS

1: Headband
3: Welding Mask
10: Adjustable Band
30: Supporting Band
31: First Supporting Band
33: Second Supporting Band
50: Length Adjusting lever
50a: Lever
70: Cushion Case
71: Mounting Member
71a: Vent Groove
73: Elastic Member
73a and 73b: Elastic Holes
75: Cushion Member
75a: Vent Portion
76: Bent Portion
77: Cushion Portion
78: Rib.

The invention claimed is:

1. A headband including an adjustable band configured to be worn on a head of a wearer and adjustable in length, a supporting band connected to the adjustable band and configured to support a top of the head of the wearer, and a length adjusting lever configured to adjust a length of the adjustable band, comprising:

a cushion case including an elastic material extends from the length adjusting lever and is integrated therewith and comprising a mounting member formed at an inner surface of the length adjusting lever and an elastic member formed at an edge of the mounting member, a cushion member including an elastic material and a vent portion formed at a center thereof is provided at an inner surface of the cushion case, and is formed in a shape corresponding to the mounting member and the elastic member of the cushion case, wherein at least one elastic hole is sequentially formed at both sides of the elastic member of the cushion case in a longitudinal direction thereof to pass therethrough, and is configured to come into contact with an occipital region of the wearer when the headband is worn, and in the cushion case, a bending modulus R1 formed at both ends of a center thereof in a longitudinal direction thereof is formed to be greater than a bending modulus R2 formed at both ends of a lower portion in the longitudinal direction, or the elastic member is formed at the mounting member to be bent in an L shape.

2. The headband claim 1, wherein at least one elastic hole is formed at the elastic member to pass therethrough, and is configured to come into gradual contact with an occipital region of the wearer when the headband is worn.

3. The headband of claim 1, wherein a vent groove is formed at a center of an inner surface of the mounting member.

4. The headband of claim 1, wherein a cushion portion is formed to protrude in a U shape at each of both sides of a center of the vent portion of the cushion member.

5. The headband of claim 1, wherein at least one rib is formed to radially protrude at a position in the cushion member corresponding to a position of the elastic member.

* * * * *